United States Patent [19]

Neuburger

[11] Patent Number: 5,065,140
[45] Date of Patent: Nov. 12, 1991

[54] EARLY WARNING REACTIVE GAS DETECTION SYSTEM

[75] Inventor: Glen G. Neuburger, Jackson Township, Hudson County, N.J.

[73] Assignee: Bell Communications Research, Inc., Livingston, N.J.

[21] Appl. No.: 666,336

[22] Filed: Mar. 8, 1991

[51] Int. Cl.$^5$ ............................................. G08B 17/10
[52] U.S. Cl. .................................. 340/634; 73/23.31; 73/24.04; 324/71.5
[58] Field of Search ...................... 340/632, 633, 634; 73/23.31, 24.01, 24.04, 24.06; 324/71.5

[56] References Cited

U.S. PATENT DOCUMENTS

| | | | |
|---|---|---|---|
| 3,253,219 | 5/1966 | Littler | 324/17 |
| 4,745,399 | 5/1988 | Kimura | 340/632 X |
| 4,782,334 | 11/1988 | Meaney | 340/634 |
| 4,947,677 | 8/1990 | Frye et al. | 73/38 |

OTHER PUBLICATIONS

"Detection of Ambient Hydrogen Chloride with a Zinc–Coated Piezoelectric Crystal Resonator Operating in . . . Different Mode", G. G. Neuburger, Anal. Chem., vol. 61, No. 14, pp. 1559–1563, Jul. 1989.

"Smoothing and Differentiation of Data by Simplified Least Squared Procedures", A. Savitsky et al., Anal. Chem., vol. 36, No. 8, pp. 1627–1639, Jul. 1964.

"Detection of Hydrogen Chloride Gas in Ambient Air with a Coated Piezoelectric Quartz Crystal", J. Hlavay et al., Anal. Chem., vol. 50, No. 7, pp. 965–967, Jun. 1978.

Primary Examiner—Jin F. Ng
Assistant Examiner—Jeffery A. Hofsass
Attorney, Agent, or Firm—Leonard C. Suchyta; Lionel N. White

[57] ABSTRACT

A reactive gas detection system provides early warning of gas emissions that often occur in developing fire conditions in environments such as telephone system central offices where halogenated substances, for example polyvinyl chloride wire insulation and brominated fire retardant materials, are prevalent. Multiple microbalance detectors (122) comprising quartz crystal oscillators coated with a layer of zinc or zinc compound are distributed about a premises and the rate of change of crystal oscillation frequency is cyclically monitored by a frequency counter (130) under control of a data processor (112). The detectors are specifically reactive to the halogen acid gases emitted during pyrolysis of the noted substances and exhibit a significant differential frequency change in the presence one or more of these gases well in advance of the outbreak of flame, smoke, or other normally detectable combustion products. In order to maintain a high rate of system monitoring, the cycle period of each frequency measurement is greatly reduced during normal conditions, with resulting low measurement resolution. Upon the occurrence of a significant threshold frequency change in any of the detectors, subsequent frequency measurements are preferentially taken at the suspect detector over an extended cycle period with high resolution to confirm that the threshold is being exceeded. Continued excessive excursion of measured frequency change beyond a preset limit initiates the generation of an alarm signal.

24 Claims, 5 Drawing Sheets

EARLY WARNING REACTIVE GAS DETECTION SYSTEM

BACKGROUND OF THE INVENTION

The present invention relates to the early detection of event conditions which include a change in the amount of a reactive gas, such as hydrogen chloride (HCl) or another of the halogen acids, in the event environment. An increase in such a gaseous constituent is typical, for example, when a fire occurs amidst electrical and electronic equipment where the use of polyvinyl chloride (PVC) wiring insulation and halogenated fire retarding adjuncts are prevalent, as in a telecommunications central office. In such a fire, these gases alone may be to a great extent responsible for significant equipment damage due to their corrosive effect. It is therefore essential that an effective warning system for such locations be able to readily detect the presence of these gases, since they will often accumulate and initiate equipment damage well prior to any onset of and at some distance from the area of actual conflagration.

The various conventional fire detectors which are currently in use generally respond to an increase in the concentration of particulate matter generated by fire conditions. The size and amount of this particulate matter that is evolved during pyrolysis or combustion of most fuel materials will depend to a great extent upon the conditions of the fire as well as on the chemical makeup of the fuel. As a result, the types of detectors and their methods of measuring the particles generated by fires will vary widely.

For example, ionization detectors employ a radioactive source, usually an alpha emitter, which causes ionization of air in a sensing chamber. When ionized, the charged molecules are accelerated toward a polarized electrode, thereby causing the flow of an electrical current. Smoke or other particulate combustion products entering the chamber cause a notable change in the ionization current. Owing to this manner of operation, ionization detectors are more responsive to small particles, typically less than 1 micrometer, and are thus effective in the presence of flaming fires.

Photoelectric detectors, on the other hand, are typically based on the effect of the combustion particles in causing the scattering of light which is normally transmitted across a detection chamber. The increase in intensity of diverted or scattered light is measured by a photodetector placed at an angle from the transmitted light beam. Since large, non-light-absorbing particles scatter light more effectively, these detectors are more responsive to such large particulate matter, typically of a diameter greater than about 1 micrometer. As a result, these detectors tend to be more effective with smoldering fires or fires in materials which burn inefficiently, since under these conditions large particles are predominantly emitted during pyrolysis or combustion.

Optical beam detectors are somewhat similar, but are based on a reduction in the intensity of light emitted from a source and measured by a photodetector located in the light path. This path is often quite long, since the source and detector are commonly mounted on opposite walls of a room under surveillance. Smoke or other combustion products moving into the light path cause either an absorption or obscuration reduction in the intensity of light reaching the photodetector.

Notably lacking among these devices, however, are systems employing chemical detection methods, that is, systems in which a chemical sensor is used to detect an increase in the ambient concentration of gaseous constituents, such as CO, $CO_2$, HCl, HBr, and the like. Although studies of telecommunications central office fires have established that a primary cause of extensive electrical equipment damage is the corrosive effect of halogen acid gases generated by thermally decomposing PVC cable and wire insulation and treated circuit boards, few chemical fire detectors are commercially available which would aid in the mitigation of such damage. A lack of commercial systems of this type is, for the most part, apparently due to the poor specificity or reliability of existing chemical sensors or sensing systems, as well as the unfavorable economics for their widespread use.

A number of gas analysis techniques are known by which a reactive gas such as HCl might be identified, but few of these have found practical application in fire detection devices. Gas trapping combined with coulometric, titrimetric, or colorimetric analysis, for example, has limited specificity and involves extended procedures which defeat near real-time measurement and response. Infrared absorption spectroscopy and indirect chemiluminescence have shown some improved selectivity and response time; however, these capabilities are still significantly short of practical levels and the costs of implementing and maintaining fire detection systems incorporating these sensor types remain prohibitive.

There are currently some commercially available systems for detecting HCl, for example, which employ sensors based upon electrochemical methods of analysis. These amperometric, coulometric, and potentiometric systems generally suffer, however, from a lack of chemical specificity and often require considerable maintenance. The sensing elements are also particularly expensive and would therefore not be useful for implementation in economical, multi-detector systems. Other available systems rely upon significantly less expensive high temperature semiconductor sensors; however, these detectors suffer greatly from a lack of chemical specificity and often have extremely demanding electrical power requirements.

One area of gas-sensing technology that has exhibited significant promise, however, for use in an economical system for selective detection of reactive gases such as HCl and other halogen acid gases is that of the piezoelectric quartz crystal microbalance. Piezoelectric resonators are available at low cost and their chemical specificity can be controlled by coating with a compound specifically responsive to the presence of HCl, for example. Such use of a zinc-coated crystal resonator microbalance has been described by Neuburger (G. G. Neuburger, *Anal. Chem.*, Vol. 61, No. 14, pp. 1559–1563, July 1989, incorporated herein by reference, and has been particularly successful in the early detection of fires affecting PVC and halogenated fire retardant materials. A practical reactive gas detection system may be based upon this technology, but requires adaptive control for reliable response and economical performance.

SUMMARY OF THE INVENTION

The present invention provides effective control in an early warning detection system comprising one or more of the zinc compound-coated quartz crystal microbalance oscillators described by Neuburger in the above-noted publication. The oscillators are employed as detector elements of the system and are mounted at various locations about a building or area to be monitored. The frequency of oscillation of each of these detectors is affected by its exposure to a reactive gas, such as HCl, and changes in frequency are noted by the present control system. Upon the occurrence of an event signified by a rapid decrease in the oscillation frequency of any detector, particularly in excess of a predetermined threshold rate indicative of the presence of a significant concentration of the gas, the system initiates an alarm signal.

In its general embodiment, the invention comprises, in addition to the coated detector crystals and their associated conventional oscillator drive electronics, a data processing system which controls the sequence of cyclic detector monitoring, calculates the oscillation frequency and frequency change rate for each detector, and determines and signals the occurrence of an event condition at any of the detectors. In order to minimize the possibility of timing errors in the frequency measurement process, a programmable oscillator frequency counter comprises a dedicated clock that is separate from that of the central processing unit (CPU) of the system. Processor memory elements comprise the typical random access (RAM) and program storage (ROM) units for current system operation and include nonvolatile programmable (EEPROM) units for maintaining detector history data and the like used in determining such system parameters as detector condition and useful lifetime. Local and external communication means, such as conventional display and input keyboard devices and telecommunication ports, are also provided to assist in real-time monitoring and programming of the system, as may be required.

Operation of the reactive gas detection system entails the regular measurement of the frequency of a given oscillator crystal to detect any notable decrease resulting from the action of HCl or other halogen acid gas on the zinc compound coating of the crystal. As discussed by Neuburger in the cited article, this action promotes the formation of a hygroscopic zinc halogen salt in the coating and, even under moderate humidity conditions, leads to absorption of water at the surface of the reacted crystal coating. The resulting increase in mass at the crystal surface causes the oscillation frequency to substantially decrease. Although other atmospheric gases may similarly react with the coated zinc compound, the reaction rate of HCl and other halogen acid gases, and the hygroscopic nature of their zinc salts, are so great as to promote a frequency response that is clearly distinguishable, thus enabling the detector to be specific to these atmospheric constituents. In view of the fact that studies have shown that about half the weight of polyvinyl chloride (PVC) electrical insulating materials is lost during pre-combustion heating as chlorine in the form of HCl gas, this specific response establishes the zinc-coated crystal oscillator as a reliable detector for the early warning of such an event condition in the vicinity of these materials. Similar response is seen in the presence of HBr gas emitted from pyrolysis of retardant-treated circuit boards.

As also described by Neuburger, the use of a time differential change in oscillator frequency is the preferred means of quantifying the extent of reactive gas exposure, particular in view of the uncontrolled variables introduced in alternative frequency monitoring by the use of reference oscillators. Reliance upon the differential rate of frequency change yields other benefits in that calculating methods are readily available which account for occasional artifact excursions and which can maintain a fairly stable frequency reference base for each system detector in spite of anticipated continuous reactivity of crystal coating under ambient atmospheric conditions.

The presently preferred method of detector crystal frequency measurement establishes a time window within which the cycles of crystal oscillation for each system detector are counted. While this method requires a window of at least one second duration to achieve a frequency count resolution of one Hz, it is quite acceptable in the general monitoring process to reduce the window to an extent which will nonetheless allow the measurement resolution to remain within the range of a selected alarm differential threshold. This flexibility in frequency measurement is a particular advantage of the present invention when a number of detectors are included in the system, since a full cycle of detector monitoring, and thus the time between the indications of current conditions at a given detector, may be significantly reduced to thereby provide near real-time alerting to event conditions that include the presence of a reactive gas.

In order to effect this measurement flexibility, a frequency counter comprising the system processor includes a window time gate counter that is programmable under the control of the CPU and is variably settable to any number of alternative modes providing slow cycling for high resolution counting, as would be utilized in establishing baseline frequencies or confirming suspected alarm conditions, or rapid cycling with low resolution to achieve wide monitoring coverage during predominantly uneventful periods. In the event that an excessive gas level appears during this latter surveillance mode, the CPU selects the suspect detector for repeated frequency measurements at the high resolution counting rate for a specified number of cycles or until it is determined whether or not an event condition in fact exists. If a sufficient number of threshold excesses are confirmed, an alarm signal is initiated by the CPU for that particular detector and the surveillance mode is reinstated with the cyclic monitoring of the remaining set of detectors within the system. In this manner, isolated detector frequency excursions or artifacts are not ignored, yet are prevented from causing an unnecessary alarm.

THE DRAWING

The present invention will be described with reference to the accompanying drawing of which.

DESCRIPTION OF THE INVENTION

Figure 1:
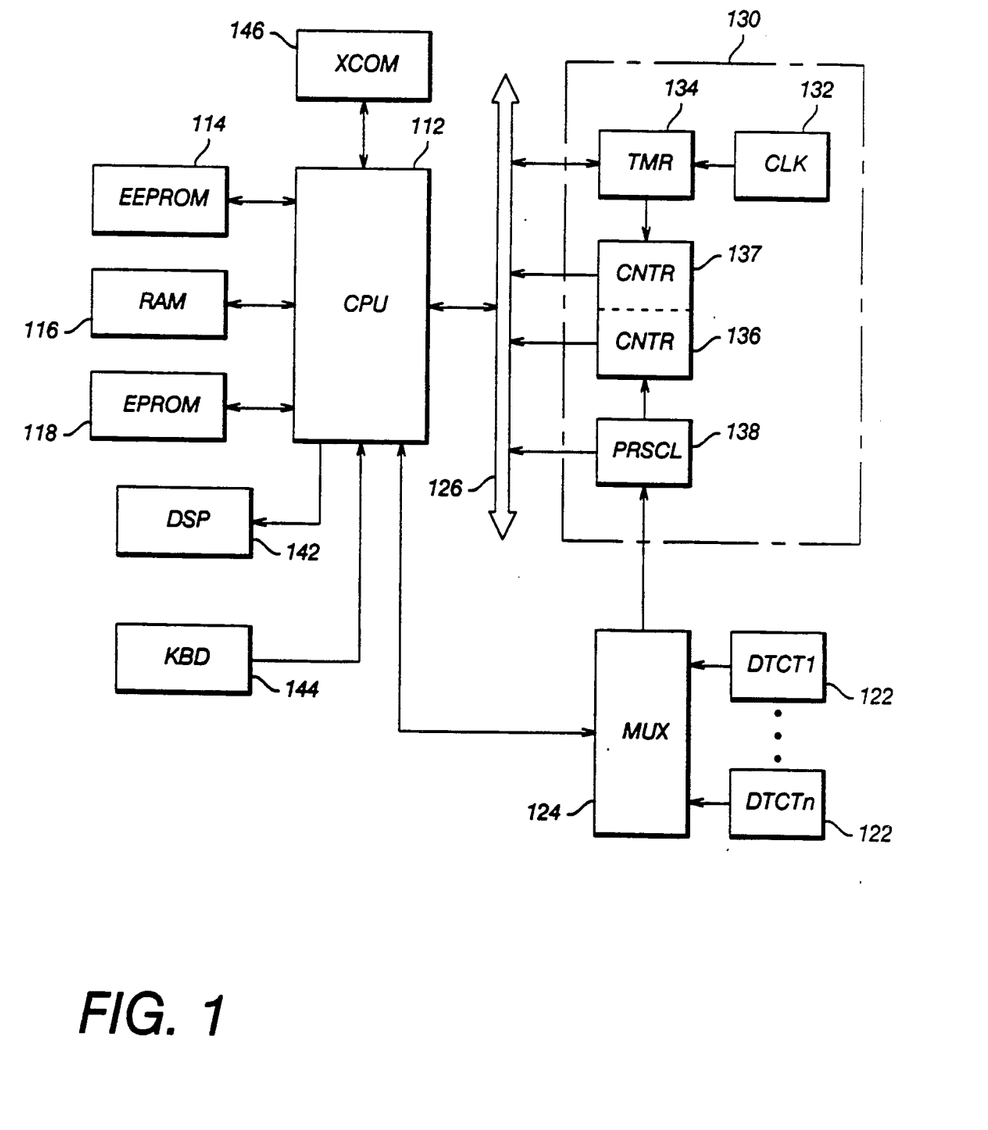
FIG. 1 a block diagram of a reactive gas detector control system embodying the invention.

An embodiment of a coated quartz crystal oscillator microbalance reactive gas detector system according to the present invention is depicted in the diagram of FIG. 1. As shown there, the system typically comprises one or more zinc-coated oscillator detectors (DTCT) 122, a frequency counter assembly 130 for measuring the frequency of the detectors, and a data processor, generally comprising central processing unit (CPU) 112, for controlling the monitoring procedures of the system, calculating individual detector frequencies and frequency change rates, and determining the occurrence of an event condition at any of the detector elements.

The detector oscillators are constructed as basically described in the previously-cited Neuburger paper and comprise commercially-available, optically-smooth, 10-MHz AT-cut quartz crystals of about 14 mm diameter having a 50–200 nm thick coating of zinc or zinc compound, selected for example from $ZnO$, $Zn_3(PO_4)_2$, and $ZnCr_2O_7$. Common deposition procedures were employed for preparing the coated crystals and generally comprised chemically cleaning the crystal surface with a $H_2SO_4/H_2O_2$ solution, rinsing with deionized water, drying in a nitrogen atmosphere, and depositing on the crystal surface, for example by a sputtering technique or the like, a film of the zinc or zinc compound coating material.

To improve adhesion of later layers to the crystal surface, a first film of about 5 nm of chromium was deposited by evaporation from a resistively-heated tungsten boat within the coating enclosure. In a subsequent coating operation in the cryogenically evacuated apparatus, a layer of about 50 nm of gold was applied to the chromium base to provide good electrical contact for the oscillator drive circuit and to establish a surface for firm adherence of the final zinc or zinc compound layer. This final coating was then applied in a similar manner to at least one surface of the pre-coated crystal. Each detector thus prepared was then electrically connected to a typical series resonance oscillator circuit and exhibited an initial frequency in its rated range of about 10 MHz.

Figure 5:
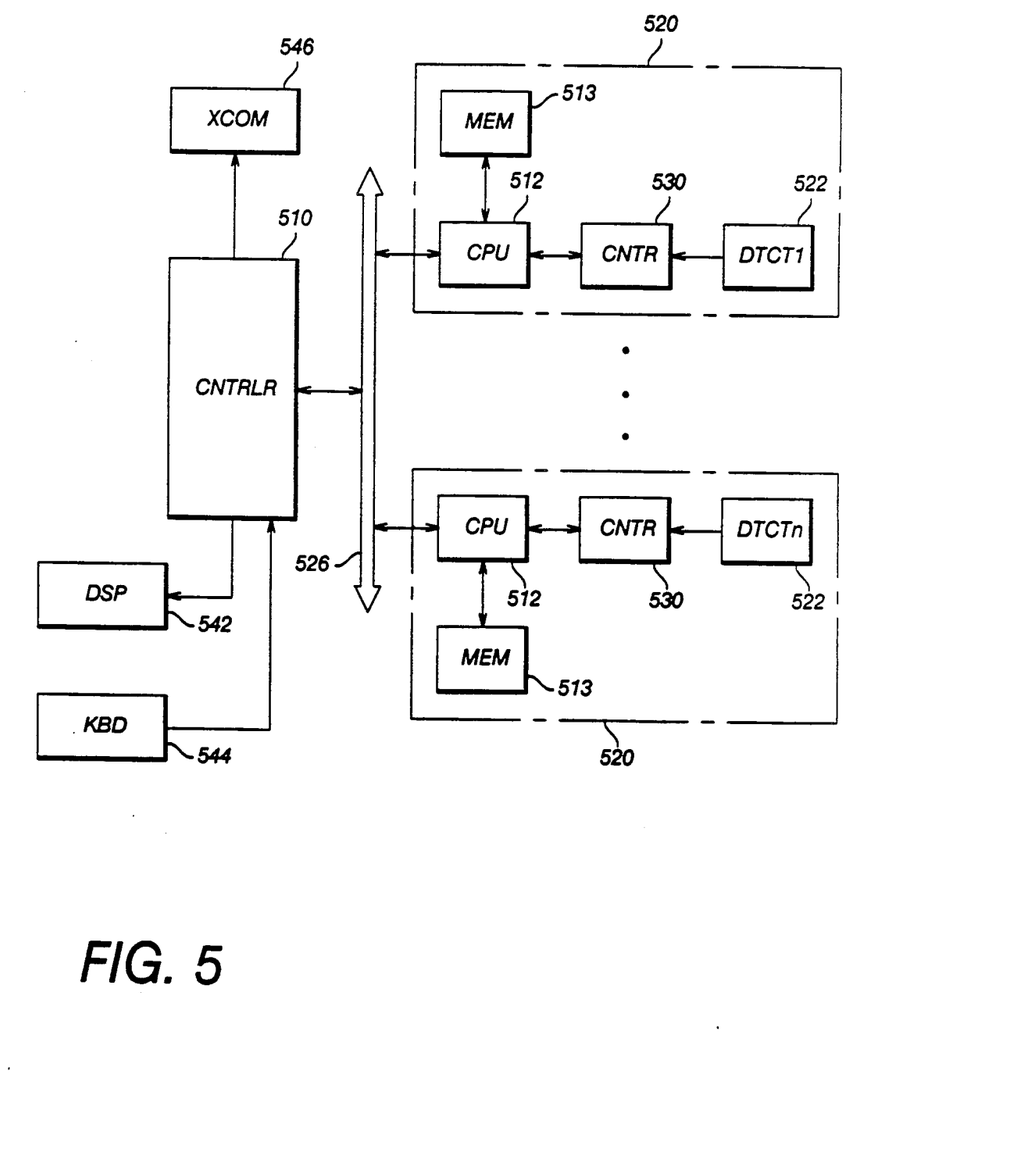
FIG. 5 is a block diagram of another embodiment of the detector control system according to the invention.

In an embodiment as shown in FIG. 1, any number of detectors 122 (DTCT1 ... DTCTn) may be mounted at convenient locations within a building or other space under surveillance. Each such detector is in communication with a frequency counter 130 which is capable of serving a plurality of detectors through a selective multiplexer (MUX) 124 under the control of CPU 112. The number of detectors in any system is entirely a matter of preference of the designer, although an upper practical limit will be reached due to the finite time required by each high resolution mode of a frequency measuring cycle, as will be noted later. At the other extreme, it would not be unusual, considering the improving economy of small scale circuitry, to have a single detector system which incorporates all necessary measuring and control elements within a stand-alone unit. A system as described here might effectively incorporate up to 500 detectors for a premises-wide coverage under centralized measurement and process management control. This higher limit could be readily achieved, for example, by employing the noted stand-alone detector units linked through a communication network with a central controller, such as shown in FIG. 5.

The described embodiment of the present system may comprise any of a number of simple commercially-available devices, such as the Intel 8052AH microcontroller with its 8-bit CPU and capability of addressing 64K bytes of external memory. This economical unit is representative of a family of 8051 devices which include additional features useful in monitoring applications, such as full duplex UART, bidirectional I/O lines, floating point operations, 16-bit timers, and local memory. These conservative features have been wholly sufficient to support multiple detectors in this effective system for identifying typical PVC fire conditions. Processors of greater speed are of course available and, primarily due to this advanced property, can readily service larger detector groupings.

Along with CPU 112 of the present system, the processor comprises operational memory units including a battery-backed EEPROM 114 serving as a non-volatile memory for the storage of critical parameters, such as initial detector crystal frequencies from which detector lifetime may be calculated despite interim losses of external system power. The remainder of memory comprises RAM 116 for scratch pad functions during system operations, and nonvolatile EPROM 118 utilized for storage of control programs. Communications between CPU 112 and operations management, whether an individual operator or a control system of broader scope, is provided by a display panel (DSP) 142 and keyboard (KBD) 144 and, to accommodate dispersed control, by remote terminal ports to external communications (XCOM) 146. The movement of data and program instructions within the system follows normal means via hardware connection or through address access, for example on bus 126.

The frequency measurements in the operation of the present embodiment employ the precision processing facilities of counter 130. Preferably this assembly comprises a stable, independent clock (CLK) 132, such as a Motorola MC145411 150 Hz bit rate generator, in order to avoid any errors or inaccuracies which might otherwise result from conflicting demands placed upon the basic CPU clock or from software interrupt functions. The 150 Hz output from this free-running clock 132 is directed to a programmable 16-bit counter 134 which conveniently comprises the first of three similar elements in an 82C54 programmable event timer device available from Intel. This first counter 134 operates as a timer (TMR) by decrementing at the 150 Hz rate of clock 132 from a programmed initial count instructed by CPU 122 via bus 126 and effects a gating interrupt at the completion of its count-down cycle. In this manner a precise time window is established during which the remaining counter elements of assembly 130 can accumulate the 10 MHz bit stream of a detector oscillator 122 to obtain a total which is conveyed via bus 126 to memory through CPU 112 to RAM 116. Each such count is retrieved at an appropriate time in a measurement cycle for determination of the current frequency of the specified detector and the extent of any recent frequency change that might indicate an event condition at that detector.

upon completion of its decrementing cycle, TMR 134 resets to the then prescribed initial count to begin a subsequent time window and at the same instant enables the remaining cascaded CNTR pair 136, 137 to begin a subsequent count accumulation cycle. This counting process is initiated for each detector 122 by channel selector instructions from CPU 112 to MUX 124. Assuming, for example, the desired measurement of the DTCT1 frequency, MUX 124 selects the channel for that detector and directs its oscillation signal into counter assembly 130. This signal is first processed in 4-bit high speed counter 138, such as a Texas Instruments 74F161 device, which is used as a divide-by-16 prescaler (PRSCL) to reduce the 10 MHz signal frequency to a range that is more compatible with the subsequent counter elements of the system. The lower frequency output signal from PRSCL 138 is cascaded into first stage CNTR 136 the output of which is likewise cascaded into second stage CNTR 137. At the interrupt that occurs upon completion of the gating cycle in TMR 134 for the specified detector, the then accumulated absolute counts in each of counter elements 136, 137, 138 are latched out in 8-bit bytes to bus 126 for storage at respective predetermined addresses associated with that detector in RAM 116.

As a result of this counting sequence in the present embodiment, the most significant bits (MSB) of the total count are provided in the first of the two bytes from CNTR 137, while the least significant bits (LSB) are in the single byte from PRSCL 138. In order to conserve memory and process time, and thereby maintain the economy of the system, the absolute current count registered in memory after a given frequency counting cycle, as previously noted, is the total of accumulated counts to that time. That is, counters 136–138 are not reset to a prescribed initial count before each cycle in order to obtain an actual frequency count during that cycle. As will be discussed later in greater detail, this procedure allows continuous cycling of frequency counting, since it relegates the determination of elapsed frequency count to a simple subtractive calculation between sequential absolute values. This calculation may readily be accomplished in CPU 112 during the ensuing required gate time period.

The surveillance and reactive gas detection process of the invention may now be seen from the following FIGS. in view of the foregoing description of a simple embodiment of the system. From a startup at 212 in FIG. 2, the program in EPROM 118 is implemented in CPU 112 to next initialize a number of specified system variables, e.g. by zeroing alarm level counters, at step 214. System parameters, such as threshold levels and gate times, are then set, at step 216, with default values specified in the process program or, alternatively, with values that may be specified by an operator through the facility of KBD 144 or XCOM 146. The previously-noted counter elements of assembly 130 are then purged, at step 218, in a procedure that entails running a few frequency counting cycles to establish a known count level at the respective memory addresses that are provided for storage of the outputs of each of counters 136–138. A sufficient number of such cycles are repeated to provide a reasonable assurance that the count cycling is stabilized and that the current stored count will provide a reliable initial value. During this purge cycling, and in the manner of actual operation, each subsequent counter output byte displaces in memory the previous count byte from which the transpired count is mathematically determined.

Figure 2:
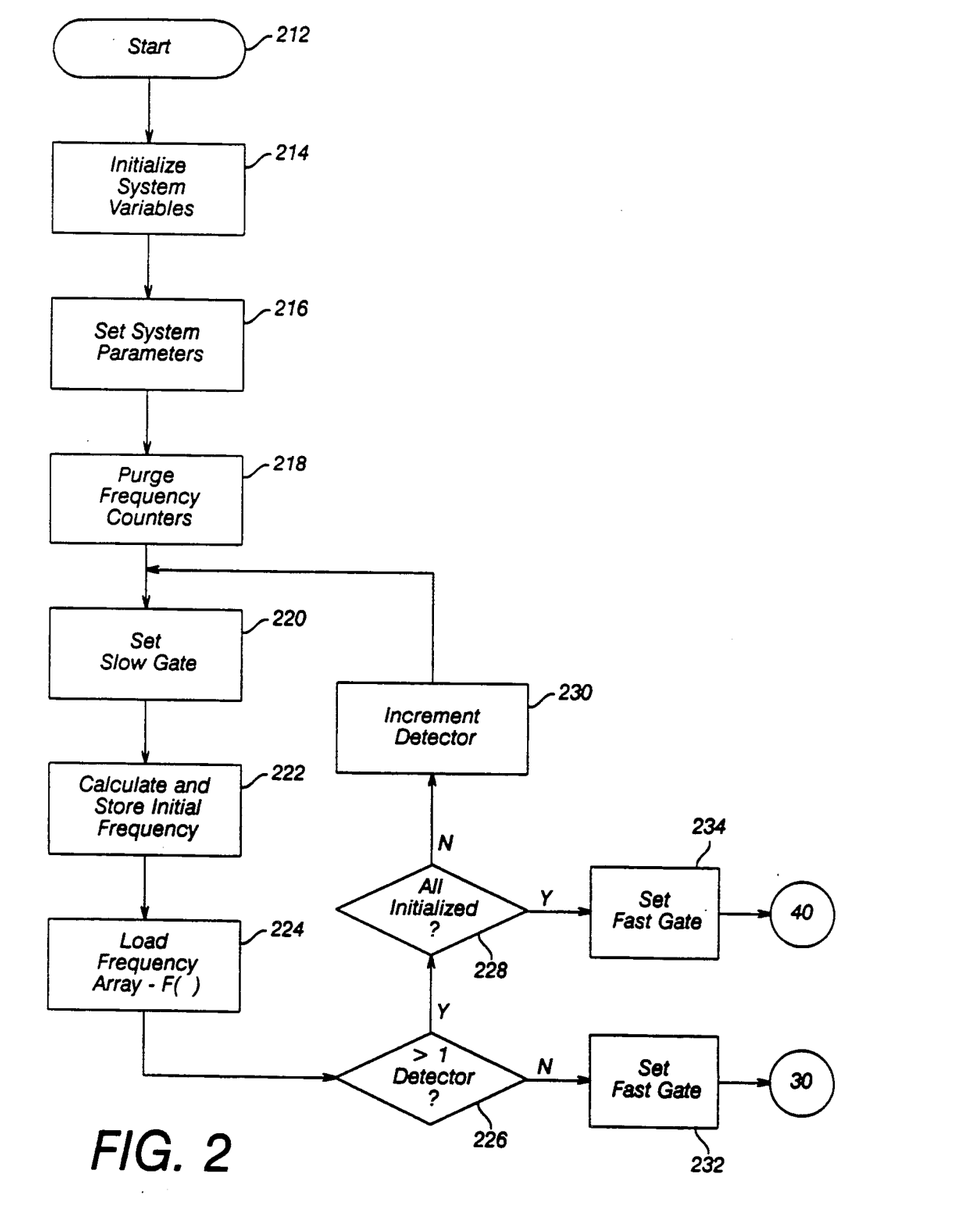
FIG. 2 is a flow diagram of the initialization phase of a program controlled process according to the invention.

The first of a number of gating modes is then set in TMR 134. While any number of such modes, and thus lengths of counting time windows, may be programmed into TMR 134 from CPU 112, it will be sufficient for the sake of this description to simply consider a fast gate and a slow gate. When the slow gate is selected, the initial count of decrementing timer 134 is set, for example, to 150 which, considering the 150 Hz frequency of CLK 132, will provide a relative slow time window of precisely one second in TMR 134. This counting cycle duration is the minimum that will enable a direct frequency count of the oscillation signal for a detector 122 without resort to a scaling factor. Thus, a total count from elements 136–138 will indicate the detector frequency in Hz to the least significant count. Although such a slow gate provides high resolution in frequency calculation, it presents the disadvantage that a whole second of time must pass before the necessary data are obtained. This requirement, coupled with the one to two seconds needed for overhead computation, may lead to an unacceptable delay in the cycling surveillance of a premises, particularly when the system comprises tens of detectors.

One aspect of the invention addresses this concern in providing for the selection of a fast gate which in essence is determined by a programmed reduction in the initial decrementer count in TMR 134. Setting this count to 15, for example, would reduce the count accumulation time window to 0.1 second and would result in a significantly faster surveillance cycle for a multiple detector system. An appropriate factor would need be applied to each accumulated count, of course, with a commensurate loss of precision in the computed frequency. During a fast gate rapid surveillance, however, this coarse measurement is sufficient to detect a differential frequency change within the range of a designated alarm threshold. As will be discussed later, such an initial alert during a fast gate cycle will immediately call into play at least one confirmatory high resolution slow gate frequency measurement cycle at the suspect detector.

The initializing phase of the process continues according to FIG. 2 for the first detector in the system with the calculation, at step 222, of the initial frequency of its crystal oscillation. This is accomplished by simply recording the frequency count of the current slow gate cycle and subtracting the count obtained in the immediately preceding cycle. A multiple of such baseline counting cycles may of course be run if desired. However obtained, the initial detector frequency is stored in non-volatile EEPROM 114 for the life of the detector. Such a useful lifetime is determined according to the desires of the system operator and is specified during the setting of system parameters, at step 216, as the acceptable limit for the reduction in detector oscillation frequency. From theoretical and experimental consideration of the effect of HCl on zinc-coated crystals it appears that a maximum reduction in frequency over time in the range of 5 to 30 KHz can be tolerated without affecting system function and sensitivity. Under ambient, non-alarm conditions this variation equates to a useful detector lifetime of greater than about 2.5 years.

As noted in the cited Neuburger paper, the present detection process eliminates the unreliable use of reference crystals by constantly calculating the differential detector frequency, i.e. the change in frequency, normally a decrease for proper system operation, at each measuring cycle and comparing such differential to a preselected threshold limit. In this manner, the slow change in frequency which unavoidably occurs due to the action of normal ambient atmospheric components on the zinc or zinc-compound coating is constantly accounted for by the cyclic updating of a baseline frequency. Thus, only significant, moderate to high rate frequency changes indicative of event condition or artifacts resulting from physical damage or crystal failure, for example, will register as a notable occurrence. In preparation for this differential calculation, which in the present embodiment follows the simplified least squares procedure described by A. Savitsky et al., *Anal.*

*Chem.*, Vol. 34, No. 8, July 1964, incorporated herein by reference, an array, F( ), of nine consecutive frequency measurements is load into memory, at step 224. This array will be constantly updated with each frequency measuring cycle and will base the frequency differential calculation.

Figure 3:
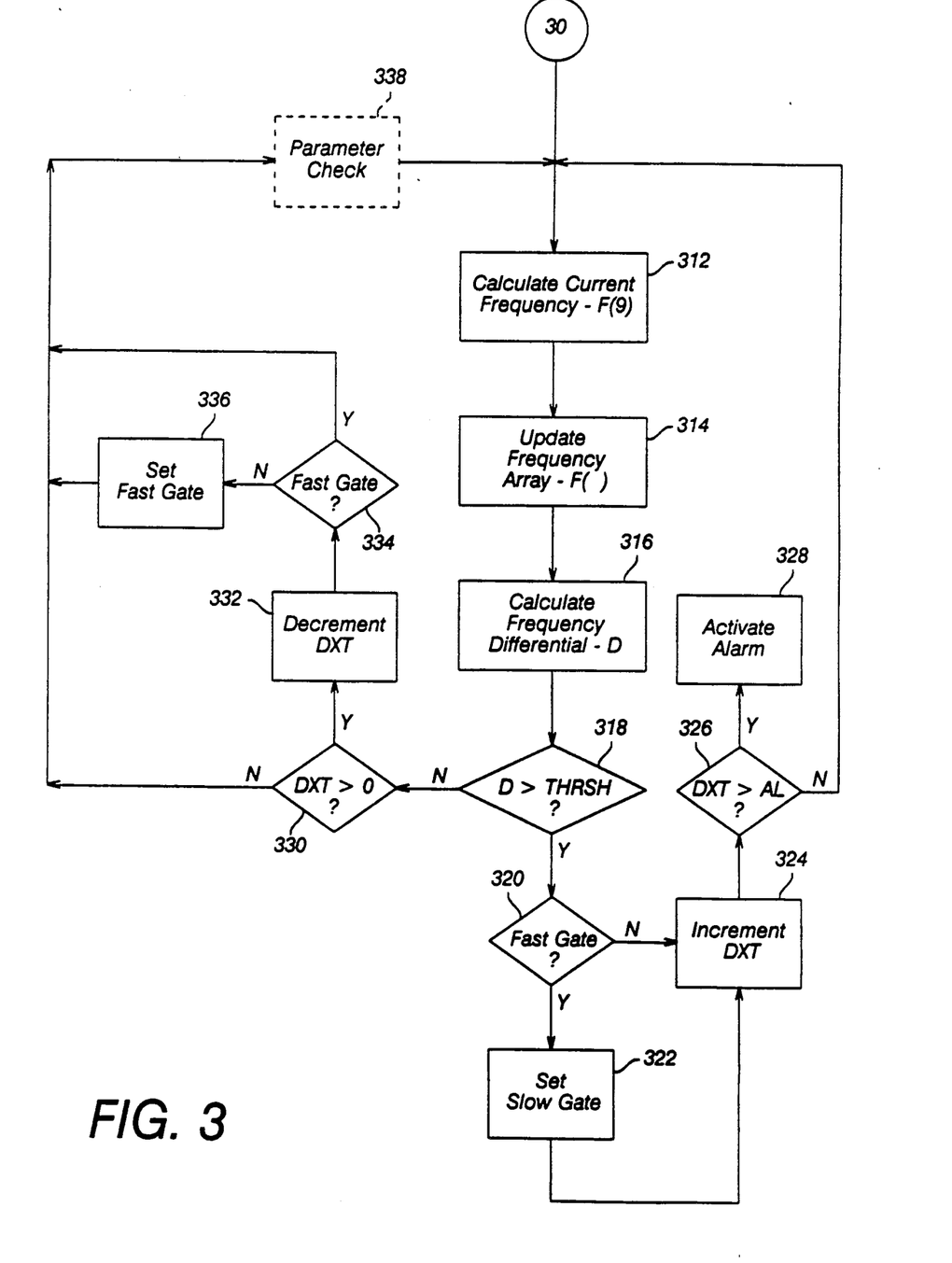
FIG. 3 is a flow diagram of the monitoring phase of a program-controlled process according to the invention in a system comprising a single detector.

As determined at step 226, if the system comprises a single detector the surveillance process will proceed through step 232, where the fast gate is set to shorten the count cycling time as previously explained, to point 30 in FIG. 3. Otherwise, each additional detector in the system will be initialized in the described manner by advancing the active channel in MUX 124 to increment the observed detector, at step 230, until all detector frequency arrays are populated and the process can proceed through a fast gate set 234 to point 40 in FIG. 4.

The operation of a single detector embodiment of the system is depicted in FIG. 3 and follows after initialization with a calculation of the current frequency, F(9), at step 312. In view of the fact that the system is in the fast gate mode, the full frequency count is not obtained. Rather, the count is scaled down to the extent that the programmed time window in TMR 134 has been reduced and thus requires a factoring to yield a coarse frequency determination. This simple calculation may be readily carried out in CPU 112 as:

$$F(9) = 150/G$$
$$(C1 + 16(C2 + 256(C3 + 256(C4 + 256(C5)))))$$

where G is the gating count set in TMR 134, and C1–C5 are the respective net binary counts from counters 138, 136, 137.

This frequency measure, which will be the ninth and most recent in the array, is forwarded, at step 314, to the appropriate memory address to update the stored frequency array, F( ), with displacement of the previously oldest component, F(1). Utilizing these nine most recent frequency values, CPU 112 calculates, at 316, the smoothed frequency differential value, D, according to Savitsky et al.

$$D + S/350;$$

where $$S = 6(F(1) - F(9)) + 21(-F(2) + F(8)) + 45(1$$
$$F(3) + F(7)) + 44(-F(4) + F(6))$$

It should be noted that the resulting differential value, D, is that which corresponds to the fourth previous measuring cycle, i.e. F(5) in the current frequency array. Thus, the determination of any event condition is slightly delayed from real time by four measuring cycles, a fact that emphasizes the utility of a fast gate mode in reducing cycle duration. Also considered in the determination of D are any changes in the time between frequency counting cycles that would be occasioned by shifts between fast and slow gates. In this respect, the sequential time of the starting of each counting cycle at a given detector is stored in memory for later use in calculation of the frequency differential, D, for that detector. As will be seen, this consideration could have particular relevance in multiple detector systems.

The frequency differential value, D, is then compared, at 318, with a preset threshold value, THRSH, e.g. about 20 Hz/sec, selected as desired from experimentation or other factors and set as a system parameter during the initialization process. Another parameter employed in the region of the process is the alarm limit, AL, which when set at the value of 10, for example, will require that an accumulation of 10 DXT, i.e. differential values in excess of THRSH, be reached before an alarm signal is transmitted by the system. In this manner, occasional differential excursions or artifacts will be prevented from initiating false alarms. In the event that THRSH is not exceeded the process will proceed through step 330, which determines the status of previous near term excursions, to occasional or optional parameter check step 338 and then to repeat the surveillance cycle with a new frequency calculation at 312. The parameter check at 338 may be performed at each cycle or after a predetermined number of cycles, as desired, and can include, for example, a review of the remaining detector lifetime by comparison with the stored initial frequency.

In the event that the THRSH comparison at 318 indicates an excursion, an enquiry, at 320, will determine the present gate mode in order that the ensuing measurement cycle will be conducted at a high resolution, slow gate speed, set at 322 if necessary, for the purpose of obtaining a confirmatory frequency measurement. In either event, the excursion is recorded by incrementing by one the DXT count at 324. If the DXT count exceeds the AL value, e.g. 10 in this example, an alarm signal is initiated by CPU 112; otherwise the next measurement cycle begins at 312. If the frequency differential continues to exceed THRSH, as in an actual event condition, DXT will continue to be incremented to the critical alarm limit, AL. An artifact, however, will not likely appear at the next cycle and the enquiry at 318 will allow the process to decrement by one the DXT counter through steps 330, 334 and return to a fast gate surveillance mode.

Figure 4:
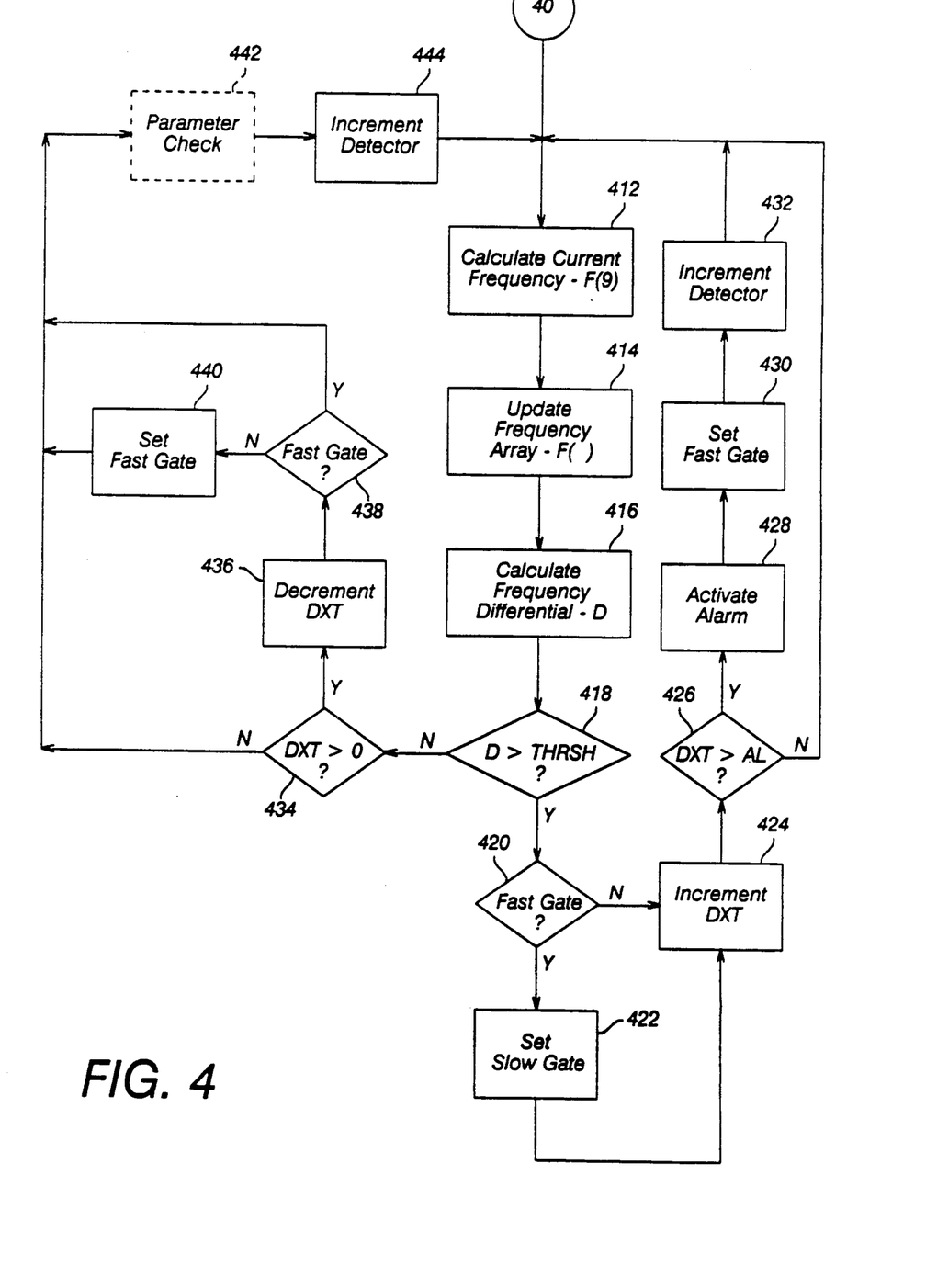
FIG. 4 is a flow diagram of the monitoring phase of a program-controlled process according to the invention in a system comprising a plurality of detectors.

Operation of a multiple detector system, as depicted in FIG. 4, follows generally the process described above with the added provision for maintaining appropriate surveillance of all detectors despite a possible alarm condition at one location. In this respect, an initial alert at a detector will be immediately investigated by a slow gate measurement set at 422, but unless the condition persists for the required 10 excursions to activate an alarm, the first negative response to the enquiry at 418 will cause the system to decrement the DXT counter only one time before moving into a fast mode to monitor the next detector with the incrementing at 444. If an alarm is initiated, the system will abandon that detector through steps 430, 432 to likewise monitor other detectors in sequence. In this manner, the system will extend first priority to a detector that continues to exhibit a present emergency, yet will provide service to the remaining system, as well, if there is an indication of recovery or alarm in that detector. An additional fail-safe parameter, not shown, might advantageously be included in a system to cause bypass of any detector registering, as in the event of crystal malfunction, sudden frequency excursions of, for example, $\pm 10^5$ Hz beyond the nominal frequency range.

Another embodiment of the invention which was mentioned earlier, i.e. a controlled network of self-contained detector systems, is depicted in FIG. 5. As shown there, the system comprises a central controller (CNTRLR) 510, itself comprising a computer with memory and programs to monitor cyclically, or according to some other prescribed or demand sequence, the respective conditions of dispersed detector systems 520 via digital bus 526. I/O elements, such as DSP 542 for displaying individual parameter states and KBD 544 for entering specific requests may be included as with the embodiment of FIG. 1. Each of detectors, DTCT1 ... DTCTn, 522 comprises an element of an individual system in which CNTR 530 comprises and performs the functions of the elements of counter assembly 130, shown in FIG. 1, while CPU 512 with its memory (MEM) 513 carries out, in the same manner as computer combination 112–118, the frequency measuring and control process depicted in FIG. 3. The initializing phase of the system procedure might be retained with the individual control of each local unit 520, or could be relegated to the general control of CNTRLR 510. Likewise, the alarm condition monitoring and detector unit selection functions of FIG. 4 might be accomplished by CNTRLR 510 or divided between CNTRLR 510 and CPUs 512.

Although the discussion of preferred embodiments of the invention has considered, for the most part, the detection of events of pyrolytic emission of reactive gas, as could occur in the incipient stage of a fire, it should be apparent that the system would be equally effective in alerting to the presence of an inordinate amount of reactive chlorine or other halogen or halogen acid gas occurring, for example, as leakage from chemical storage or processing facilities. Also, other detector coating materials specific in their reaction to different atmospheric constituents might likewise be employed in this system to alert to the presence of such constituents and to the conditions that result from their presence.

In addition to the variations in structure and process suggested above, it is anticipated that other embodiments of the present invention, such as hardware or firmware implementation of the indicated software process instructions, will also undoubtedly occur to the skilled artisan in the light of the foregoing description. Such embodiments are likewise intended to be encompassed within the scope of the invention as recited in the following claims.

What is claimed is:

1. A system for signaling the occurrence of an event having associated therewith the presence of a specified gas in the environment of said event, which system comprises a quartz crystal microbalance detector having a coating thereon comprising a composition reactive in the presence of said gas to effect a change in the oscillation frequency of said detector, data processing means communicating with said detector, and program means communicating with said processing means and comprising instructions for said processing means to repeatedly measure said detector frequency, to determine a detector frequency change rate upon subsequent measurements of said frequency, and to initiate an alarm signal in response to a frequency change rate excursion beyond a predetermined threshold frequency change rate characterized in that said program means further comprises instructions for said processor to:
   a) establish an alarm limit count specifying a minimum number of said beyond threshold excursions required before said alarm signal is initiated;
   b) increment by one a count of said excursions upon determining a frequency change rate that exceeds said threshold;
   c) decrement by one said excursion count, to a minimum of zero, upon determining a frequency change rate that does not exceed said threshold; and
   d) initiate said alarm signal when said excursion count exceeds said alarm limit count.

2. A system according to claim 1 characterized in that said program means further comprises instructions for said processor to measure said detector frequency:
   a) at a higher resolution upon determining a frequency change rate that exceeds said threshold; and
   b) at a lower resolution upon determining a frequency change rate that does not exceed said threshold.

3. A system according to claim 2 characterized in that said processing means comprises detector oscillation counting means and said program means further comprises instructions for said processing means:
   a) to measure said detector frequency by determining the number of oscillations of said detector that occur within a specified time span; and
   b) to specify said time span as:
      1) a first time span to yield said lower resolution frequency measurement, or
      2) a second, longer time span to yield said higher resolution frequency measurement.

4. A system according to claim 1 characterized in that
   a) a multiplicity of said detectors are located in said environment, and
   b) said program means further comprises instructions for said processing means to monitor said excursion count for each said detector.

5. A system according to claim 1 characterized in that a multiplicity of said detectors are located in said environment and said program means further comprises instructions for said processing means
   a) to determine the frequency change rate of each of said detectors, seriatim, until the determination of a frequency change rate at one of said detectors that exceeds said threshold,
   b) to thereupon repeatedly determine the frequency change rate of only said one detector until
      1) the determination of a frequency change rate that does not exceed said threshold, or
      2) the initiation of an alarm signal, and
   c) to then resume the seriatim determination of the frequency change rate of each of said detectors.

6. A system according to claim 1 characterized in that
   a) said specified gas is a halogen acid gas; and
   b) said detector coating composition comprises a material selected from the group consisting of zinc, zinc oxide, zinc phosphate, and zinc dichromate.

7. A system according to claim 6 characterized in that said halogen acid is selected from the group consisting of hydrogen chloride and hydrogen bromide.

8. A system according to claim 7 characterized in that said event is pyrolysis of a material comprising a halogen compound.

9. A method of signaling the occurrence of an event having associated therewith the presence of a specified gas in the environment of said event, which method comprises locating in said environment a quartz crystal microbalance detector having a coating thereon comprising a composition reactive in the presence of said gas to effect a change in the oscillation frequency of said detector, repeatedly measuring said detector frequency, determining a frequency change rate upon subsequent measurements of said frequency, specifying a frequency change rate threshold beyond which a detector frequency rate change indicates the occurrence of said event, and initiating an alarm signal in response to a frequency change rate excursion beyond said threshold characterized in that said method further comprises:
  a) establishing an alarm limit count specifying a minimum number of said beyond threshold excursions required before said alarm signal is initiated;
  b) incrementing by one a count of said excursions upon determining a frequency change rate that exceeds said threshold;
  c) decrementing by one said excursion count, to a minimum of zero, upon determining a frequency change rate that does not exceed said threshold; and
  d) initiating said alarm signal when said excursion count exceeds said alarm limit count.

10. A method according to claim 9 characterized in that said detector frequency is measured:
  a) at a higher resolution upon determining a frequency change rate that exceeds said threshold; and
  b) at a lower resolution upon determining a frequency change rate that does not exceed said threshold.

11. A method according to claim 10 characterized in that
  a) said detector frequency is measured by determining the number of oscillations of said detector that occur within a specified time span; and
  b) said time span is specified to be
    1) a first time span yielding said lower resolution frequency measurement, or
    2) a second, longer time span yielding said higher resolution frequency measurement.

12. A method according to claim 9 characterized in that
  a) a multiplicity of said detectors are located in said environment, and
  b) said method further comprises monitoring said excursion count for each said detector.

13. A method according to claim 9 characterized in that
  a) a multiplicity of said detectors are located in said environment,
  b) the frequency change rate of each of said detectors is determined, seriatim, until the determination of a frequency change rate at one of said detectors that exceeds said threshold,
  c) whereupon the frequency change rate of only said one detector is repeatedly determined until
    1) the determination of a frequency change rate that does not exceed said threshold, or
    2) the initiation of an alarm signal, and
  d) then the seriatim determination of the frequency change rate of each of said detectors is resumed.

14. A method according to claim 9 characterized in that
  a) said specified gas is a halogen acid gas; and
  b) said detector coating composition comprises a material selected from the group consisting of zinc, zinc oxide, zinc phosphate, and zinc dichromate.

15. A method according to claim 14 characterized in that said halogen acid is selected from the group consisting of hydrogen chloride and hydrogen bromide.

16. A method according to claim 15 characterized in that said event is pyrolysis of a material comprising a halogen compound.

17. A system for signaling the occurrence of an event having associated therewith the presence of a specified gas in the environment of said event, which system comprises a quartz crystal microbalance detector having a coating thereon comprising a composition reactive in the presence of said gas to effect a change in the oscillation frequency of said detector, means for repeatedly measuring said detector frequency, means for determining a frequency change rate upon subsequent measurements of said frequency, means for specifying a frequency change rate threshold beyond which a detector frequency rate change indicates the occurrence of said event, and means for initiating an alarm signal in response to a frequency change rate excursion beyond said threshold characterized in that said system further comprising:
  a) means for establishing an alarm limit count specifying a minimum number of said beyond threshold excursions required before said alarm signal is initiated;
  b) means for incrementing by one a count of said excursions upon determining a frequency change rate that exceeds said threshold;
  c) means for decrementing by one said excursion count, to a minimum of zero, upon determining a frequency change rate that does not exceed said threshold; and
  d) means for initiating said alarm signal when said excursion count exceeds said alarm limit count.

18. A system according to claim 17 characterized in that said detector frequency measuring means comprises means for measuring:
  a) at a higher resolution upon determining a frequency change rate that exceeds said threshold; and
  b) at a lower resolution upon determining a frequency change rate that does not exceed said threshold.

19. A system according to claim 18 characterized in that
  a) said detector frequency measuring means determines the number of oscillations of said detector that occur within a specified time span; and
  b) said system further comprises means for specifying said time span as
    1) a first time span yielding said lower resolution frequency measurement, or
    2) a second, longer time span yielding said higher resolution frequency measurement.

20. A system according to claim 17 characterized in that
  a) a multiplicity of said detectors are located in said environment, and
  b) said system further comprises means for monitoring said excursion count for each said detector.

21. A system according to claim 17 characterized in that a multiplicity of said detectors are located in said environment and said system further comprises
  a) means for determining the frequency change rate of each of said detectors, seriatim, until the determination of a frequency change rate at one of said detectors that exceeds said threshold,
  b) means for thereupon repeatedly determining the frequency change rate of only said one detector until
    1) the determination of a frequency change rate that does not exceed said threshold, or
    2) the initiation of an alarm signal, and
  c) means for then resuming the seriatim determination of the frequency change rate of each of said detectors.

22. A system according to claim 17 characterized in that a) said specified gas is a halogen acid gas; and
b) said detector coating composition comprises a material selected from the group consisting of zinc, zinc oxide, zinc phosphate, and zinc dichromate.

23. A system according to claim 22 characterized in that said halogen acid is selected from the group consisting of hydrogen chloride and hydrogen bromide.

24. A system according to claim 23 characterized in that said event is pyrolysis of a material comprising a halogen compound.

* * * * *

UNITED STATES PATENT AND TRADEMARK OFFICE
CERTIFICATE OF CORRECTION

PATENT NO. : 5,065,140

DATED : November 12, 1991

INVENTOR(S): Glen G. Neuburger

It is certified that error appears in the above-identified patent and that said Letters Patent is hereby corrected as shown below:

Column 6, line 56, change "upon" to read --Upon--.

Column 9, lines 42-49, change:

"Savitsky et al.

D+S/350;

where

S=6(F(1)-F(9)+21(-F(2)+F(8))+45(1
F(3)+(F(7))+44(-F(4)+F(6))"

to read:

--Savitsky et al.:

D = S/350;

UNITED STATES PATENT AND TRADEMARK OFFICE
CERTIFICATE OF CORRECTION

PATENT NO.   : 5,065,140
DATED        : November 12, 1991
INVENTOR(S)  : Glen G. Neuburger It is certified that error appears in the above-identified patent and that said Letters Patent is hereby corrected as shown below:

where

S = 6(F(1)-F(9))+21(-F(2)+F(8))+46(-F(3)+F(7))+44(-F(4)+F(6))--

Signed and Sealed this

Seventh Day of June, 1994

Attest:

BRUCE LEHMAN

*Attesting Officer*   *Commissioner of Patents and Trademarks*